United States Patent [19]
Vanderlip

[11] Patent Number: 5,892,155
[45] Date of Patent: *Apr. 6, 1999

[54] ADJUSTABLE FIXTURE FOR USE WITH A WIRE PULL TESTER

[75] Inventor: Fredrick James Vanderlip, Tempe, Ariz.

[73] Assignee: VLSI Technology, Inc., San Jose, Calif.

[*] Notice: The term of this patent shall not extend beyond the expiration date of Pat. No. 5,686,670.

[21] Appl. No.: 909,285

[22] Filed: Aug. 11, 1997

Related U.S. Application Data

[63] Continuation of Ser. No. 752,908, Nov. 20, 1996, Pat. No. 5,686,670.
[51] Int. Cl.⁶ .................................................. G02N 3/08
[52] U.S. Cl. .................................. 73/827; 73/828; 73/830
[58] Field of Search ............................... 73/827, 828, 830

[56] References Cited

U.S. PATENT DOCUMENTS

| | | | |
|---|---|---|---|
| 3,581,557 | 6/1971 | Drees | 73/827 |
| 3,759,088 | 9/1973 | Hardwick, III | 73/827 |
| 3,945,248 | 3/1976 | West | 73/827 |
| 5,341,685 | 8/1994 | Malone | 73/827 |
| 5,686,670 | 11/1997 | Vanderlip | 73/827 |

*Primary Examiner*—Max H. Noori

[57] ABSTRACT

A fixture for use with a wire pull tester that tests the strength of a bond between an electrical contact of a semiconductor device and a wire affixed to the electrical contact. The fixture comprises a device support, a mounting surface provided on the device support, and a port provided at the mounting surface. The device support may include a height adjustment mechanism. The mounting surface may be configured to engage a surface of the semiconductor device and includes a port with which an air pressure differential is produced to maintain engagement between the mounting surface and the semiconductor device surface.

24 Claims, 7 Drawing Sheets

ADJUSTABLE FIXTURE FOR USE WITH A WIRE PULL TESTER

This is a Continuation of application Ser. No. 08/752,908, filed Nov. 20, 1996, now U.S. Pat. No. 5,686,670, which application(s) are incorporated herein by reference.

FIELD OF THE INVENTION

This invention relates generally to test fixtures and, more particularly, to a fixture for holding a semiconductor device during a wire pull test.

BACKGROUND OF THE INVENTION

Increased reliance on semiconductor devices has resulted in a concomitant need for increased stringency of manufacturing quality control sceening procedures. One traditional quality control test is commonly referred to as a wire pull test. To facilitate an understanding of a wire pull testing procedure, a description of the general structure of a typical semiconductor device is provided.

A typical semiconductor device includes a die which is fabricated from semiconductor material to form electronic components and interconnects thereon. The die is generally encompassed by a casing to protect the die from damage or degradation caused by external sources. Leads, also referred to as pins, protrude externally from the casing to enable connectivity between the semiconductor device and other circuitry and components external to the device. Die bonding pads are provided on the die to couple the die to the leads. Lead pads are mounted on the casing and are connected to the leads. To provide connectivity between the die and the leads, small wires are connected between the lead pads and the die bonding pads using a wire bonding process.

Semiconductor devices are generally produced in batches or lots. A typical quality control procedure involves subjecting a number of randomly selected semiconductor devices from a particular lot to a wire pull test in accordance with a given test specification. Such a specification typically outlines the number of semiconductor devices from each lot that must be tested, and the number of wires for each semiconductor device that must be subjected to the test. As an example, one specification requires the testing of a total of fifteen wires in four semiconductor devices per lot.

A typical wire pull test is designed to assess the strength of the bonds between the wire and both the die bonding pads and the lead pads to which the wires are connected. The wire pull test is performed by accessing the die, the wires, the die bonding pads, and the lead pads, and hooking a wire pulling member of the test apparatus to a selected wire of the semiconductor device. A force is applied to the wire pulling member so as to pull the wire away from the pads. In accordance with a destructive wire pull testing procedure, the pull force is increased until either the wire breaks or the bond between the wire and either the die bonding pad or the lead pad breaks. The breaking force is then determined and recorded. If the breaking force is greater than a threshold provided in the specification, the test is considered a success, otherwise, the test is considered a failure. A typical test specification provides guidelines as to the number of tests that must be successful in order for the lot to be considered acceptable.

A typical wire pull testing apparatus includes a fixture which is used, with limited success, to support the subject semiconductor device during the test. Currently, many conventional fixtures fail to satisfactorily constrain the device during the wire pull test, often requiring manual holding of the device under test. Other conventional fixtures are constructed for use with one particular device type, thus requiring the testing facility to make available a multitude of fixtures configured for use with a multitude of device types. Performing wire pull testing using existing fixtures is often inefficient in terms of testing time and cost, due to the need for a high degree of manual intervention during each test.

SUMMARY OF THE INVENTION

The present invention is directed to a fixture that is employed to maintain engagement between a device support and a semiconductor substrate or device through the use of an air pressure differential and method therefor. The fixture is used with an apparatus that tests the strength of a bond between an electrical contact of a semiconductor device and a wire affixed to the electrical contact. The fixture includes a device support which may include a height adjustment mechanism. A mounting surface configured to engage a surface of the semiconductor device. An air pressure differential is produced at a port provided at the mounting surface to maintain engagement between the mounting surface and the semiconductor device when a pull force provided by a wire pulling member of the tester is imparted to the wire affixed to the electrical contact of the semiconductor device.

DETAILED DESCRIPTION OF THE EMBODIMENTS

Figure 1:
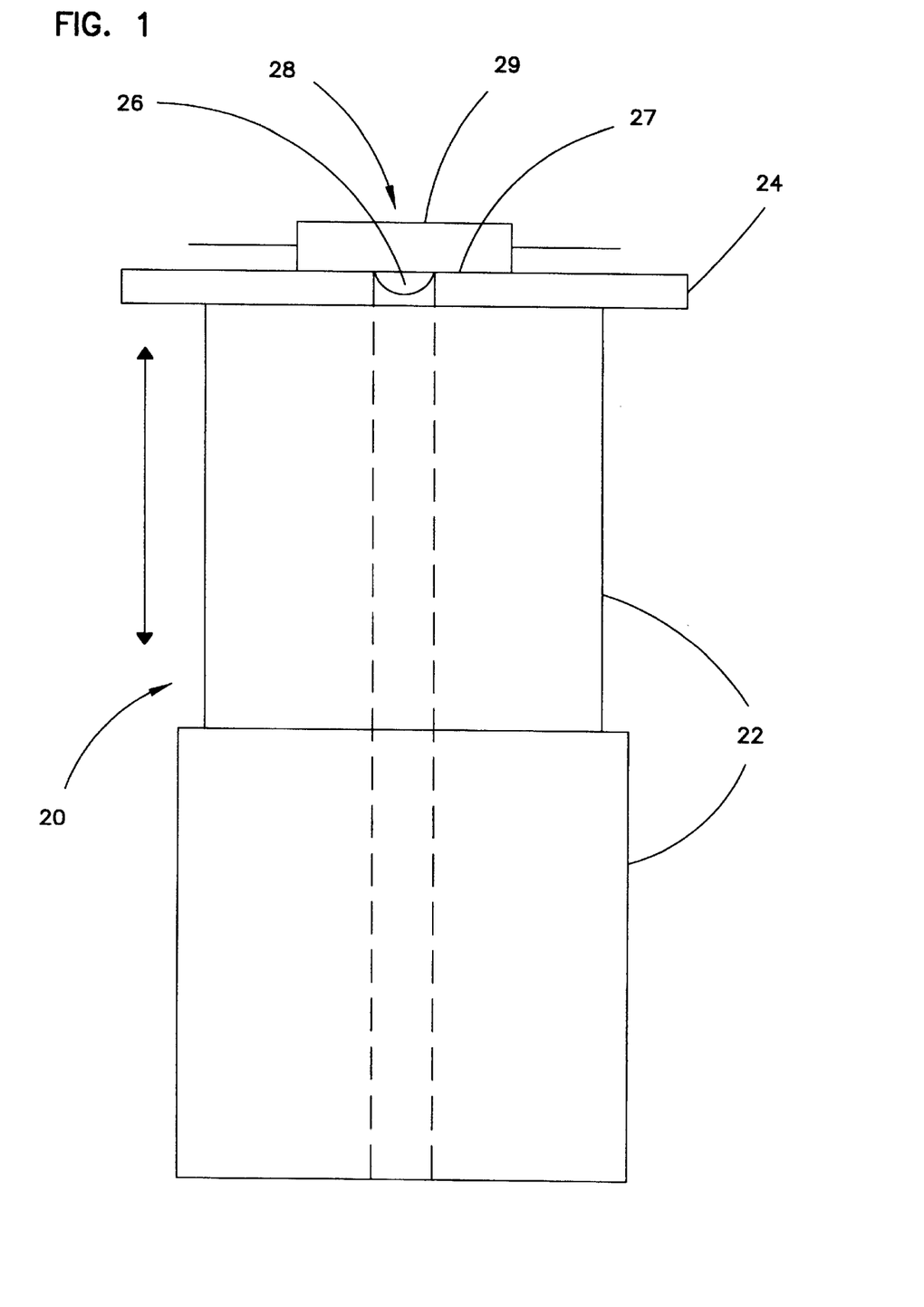
FIG. 1 is a side elevational view of a support fixture in accordance with one embodiment of the present invention.

Referring now to the Drawings, FIG. 1 shows a fixture 20 in accordance with one embodiment of the invention. The fixture 20 includes a device support 22, a mounting surface 24 provided on the device support 22, and a port 26 provided at the mounting surface 24. The device support 22 includes a mechanism for adjusting the height of the fixture 20.

A semiconductor device 28 is placed on the mounting surface 24 during the wire pull test. The semiconductor device 28 is positioned so that it covers the port 26 and is in contact with the portion of the mounting surface 24 immediately adjacent to the port 26, thereby creating a seal or partial seal between the semiconductor device 28 and the mounting surface 24 so as to restrict airflow through the seal into the port 26.

To obtain accurate test results, it is desirable that the semiconductor device 28 maintain contact with the mounting surface 24 throughout the testing procedure. To accomplish this, an air pressure differential is produced at the port 26 by use of a vacuum apparatus (not shown) coupled to the port 26. The vacuum apparatus evacuates air from the port 26, thereby reducing the air pressure at the port 26. One example of a suitable vacuum apparatus is a vacuum pump.

In general, air exerts a pressure or force against a surface with which it is in contact. Static air pressure at the port 26 exerts a force against a surface 27 of the semiconductor device 28 which tends to push the semiconductor device 28 away from the port 26. This force is opposed by a force pushing against a surface 29 of device 28 resulting from ambient air pressure at the surface 29 of the device 28. When the air at the port 26 is evacuated by the vacuum apparatus, a concomitant decrease in the force pushing against the surface 27 results. A net force applied to the semiconductor device 28 toward the mounting surface 24 is thus produced, which may be varied in magnitude to maintain contact between the semiconductor device 28 and the mounting surface 24.

Figure 2:
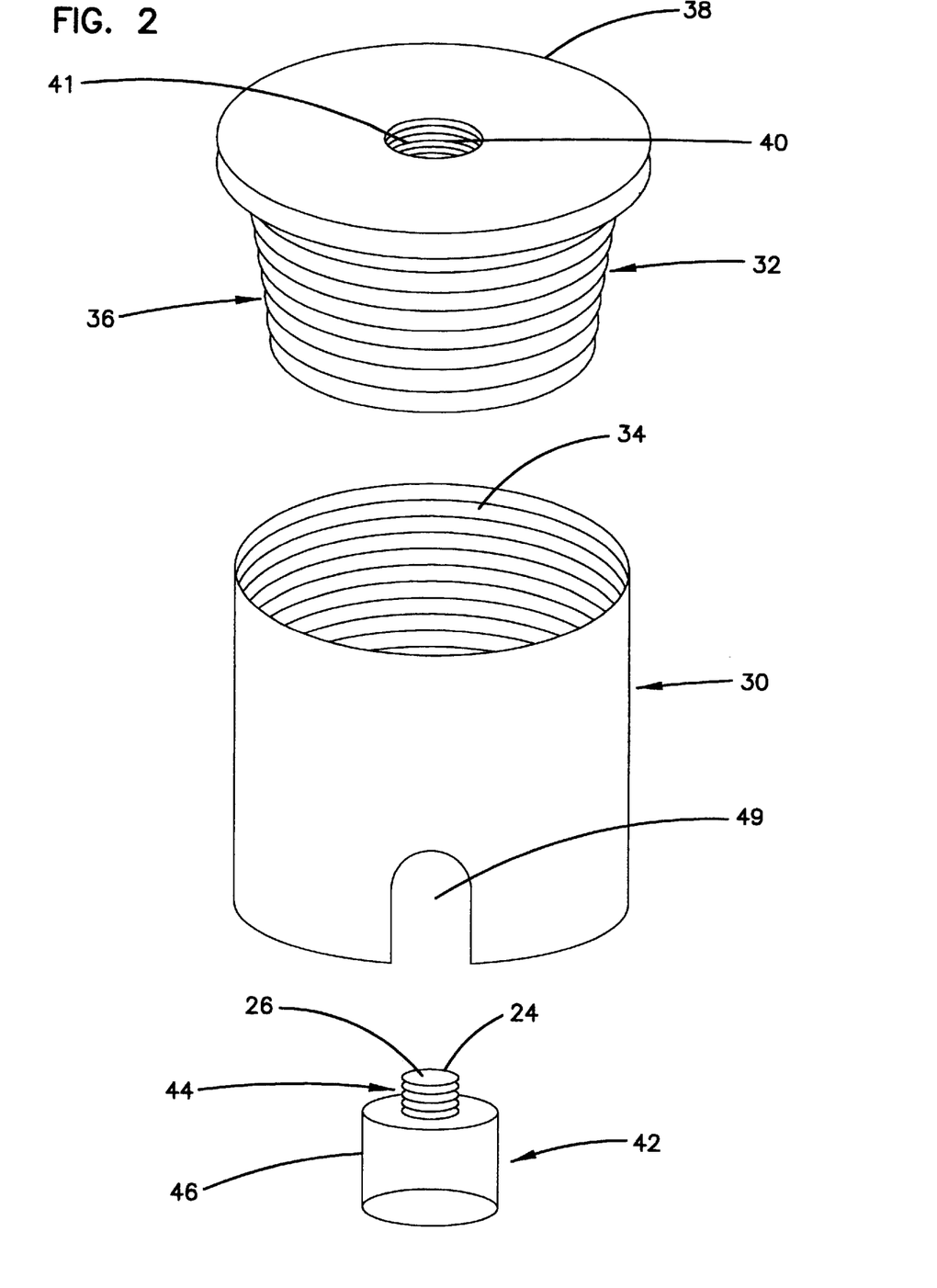
FIG. 2 is a perspective view of various elements of another embodiment of a support fixture.

One embodiment of the present invention is depicted in FIG. 2. The device support 22 in accordance with this embodiment includes a lower stand section 30 and an upper stand section 32. The lower stand section 30 may be constructed in the form of a hollow cylinder having both ends open and an inner surface 34 that is partially threaded to facilitate engagement with the upper stand section 32.

The upper stand section 32 may be constructed in the form of a hollow cylinder having an outer surface 36 that is partially threaded in the opposite direction, but with the same pitch, as the threaded inner surface 34 of lower stand section 30. The threading on surfaces 34 and 36 is configured so that the two stand sections 30 and 32 can be mated by screwing the upper stand section 32 into the lower stand section 30 to form the adjustable device support 22. The height of the fixture 20, in accordance with this embodiment, is adjusted by altering the engagement of stand sections 30 and 32 (e.g., by partially screwing or unscrewing the upper stand section 32 relative to the lower stand section 30).

In one embodiment of the invention, the fixture 20 is configured in this manner to provide for device support height adjustments ranging between approximately 2¼ inches and 2⅝ inches. Those skilled in the art will recognize that other methods and mechanisms may be employed for adjusting the height of the fixture 20. It is to be understood that the invention is not limited to the adjustment mechanism disclosed herein.

The upper stand section 32 includes an open end. The other end of the upper stand surface 32 includes a surface 38. The surface 38 includes a hole 40 bored through the center of surface 38, the hole 40 being defined by a threaded sidewall 41. An adapter 42 is configured to screw into the hole 40 provided in the upper stand section 32. The adapter 42 includes a mounting column 44 and a coupler 46 attached to the mounting column 44. The coupler 46 is coupled to the vacuum apparatus (not shown) and configured so that air can flow from the coupler 46 to the mounting column 44.

Figure 4:
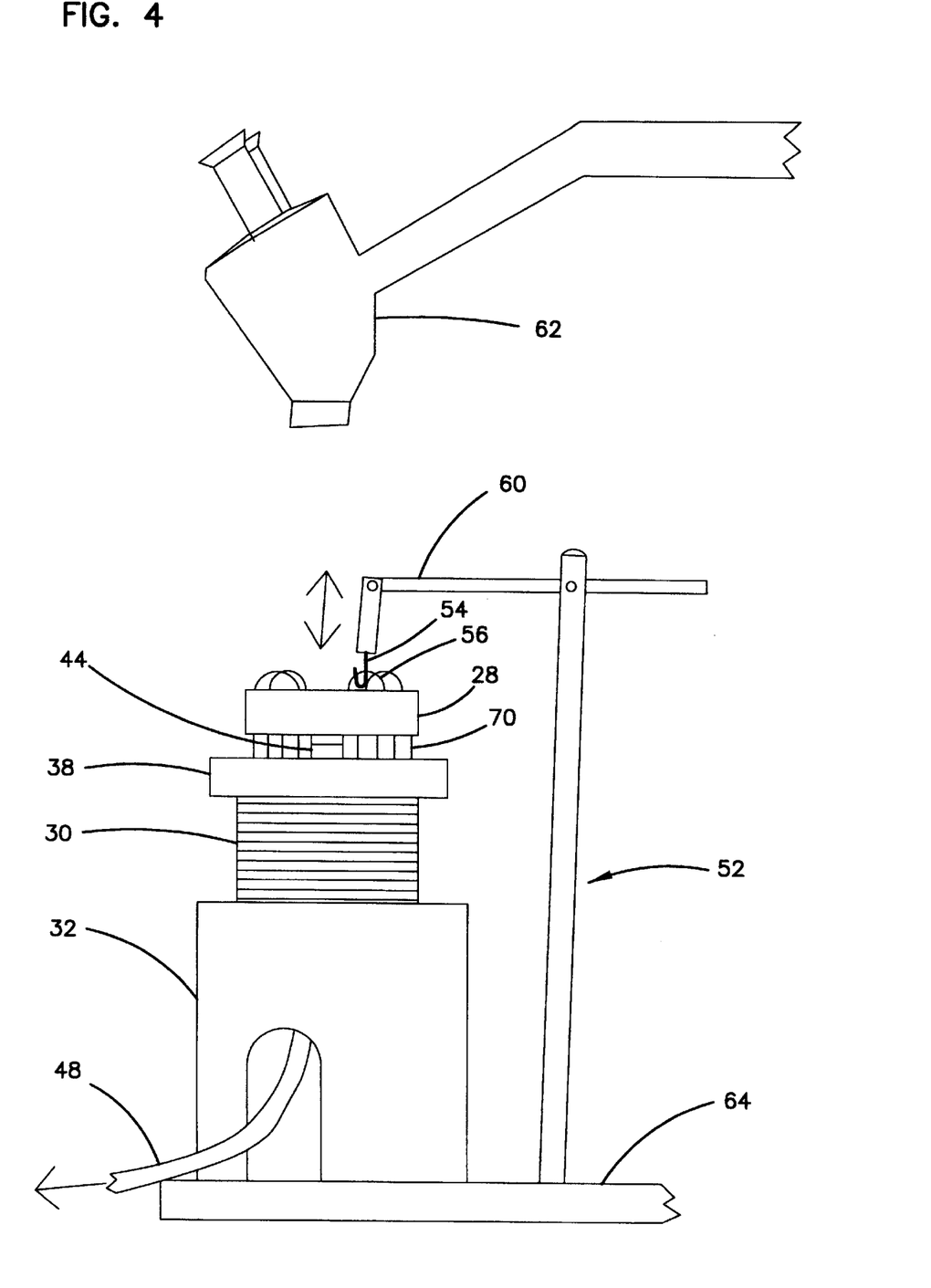
FIG. 4 is a side elevational view of a support fixture used in cooperation with a wire pull tester.

The mounting column 44 is constructed in the form of a cylinder with open ends and threading along its outer surface. The threading of the mounting column 44 is configured so that it will mate with the threading of the sidewall 41 of the upper stand section 32. The mounting column 44 is configured so that a portion of the mounting column 44 will extend beyond the hole 40 and be orthogonal to the surface 38 of the upper stand section 32 when the adapter 42 is screwed into the hole 40 from the interior of upper stand section 32, as is shown in FIG. 4. The mounting surface 24 and the port 26 are provided at the end of the portion of mounting column 44 which extends through the hole 40 and beyond the surface 38 of the upper stand section 32.

Figure 3:
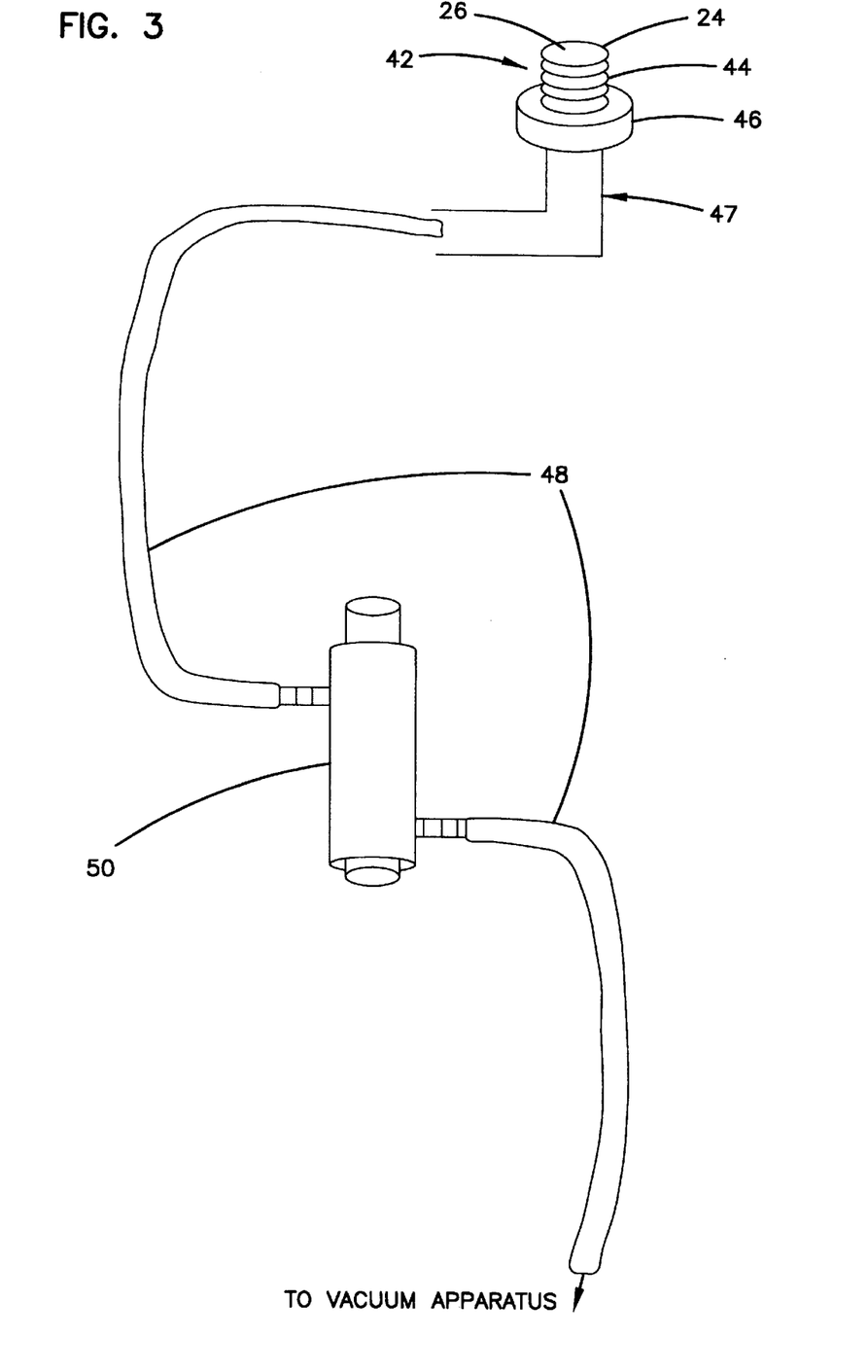
FIG. 3 is a perspective view of several elements for producing an air pressure differential at a port provided on a support fixture.

FIG. 3 depicts one embodiment of the coupling between the adapter 42 and a vacuum apparatus (not shown). In accordance with this embodiment, a fitting 46 is connected to a swivel elbow 47. The elbow 47 is connected to a flexible hose 48 which exits the fixture 20 through an opening 49 in the lower stand section 30, as is shown in FIG. 2. The swivel action of the elbow 47 allows the adapter 42 to rotate when the upper stand section 32 is screwed into the lower stand section 30 without permitting corresponding rotation by the hose 48.

In accordance with the embodiment of the invention depicted in FIG. 3, the hose 48 is interrupted by a valve 50. The valve 50 provides control over the production and magnitude of the air pressure differential produced at the port 26. The valve 50 has at least two positions, an open position and a closed position, but may also have intermediate positions. In the open position, air is permitted to flow between the port 26 and the vacuum apparatus in order to produce an air pressure differential at the port 26. As will be described in greater detail hereinbelow, the air pressure differential creates a vacuum at the port 26 which maintains engagement between the mounting surface 24 and a surface of a semiconductor device 28 situated proximate the port 26. When the valve 50 is in the closed position, the adapter 42 is isolated from the vacuum apparatus. If contact between the mounting surface 24 and the semiconductor device 28 is no longer desired, the air valve 50 can be operatively actuated to the closed position so that the air pressure differential at the port 26 is no longer continuously produced. The semiconductor device 28 can then be removed with ease from the mounting surface 24.

In an alternative embodiment, the air valve 50, in either the closed position or in an intermediate position, can be configured to permit a reduced volume of air to flow through the hose 48 and into the port 26 when full engagement force is not required, such as when removing the semiconductor device 28 from the fixture 20. This configuration is advantageous when a low or moderate degree of retention force is desired at various times during the testing procedure, such as when placing or removing the semiconductor device or substrate 28 respectively on and from the device support 22. It is noted that the components of fixture 20 are constructed of suitable materials, such as metal or plastic, which provide strength and durability. For example, the fixture 20 may be constructed from aluminum, steel, or brass.

Semiconductor devices are available in many different sizes, shapes, and configurations. An adverse consequence that results from the proliferation and diversity of semiconductor packaging technologies is the current need for different support fixture configurations required to hold each device package type during a conventional wire pull test. Using an appropriately configured support fixture is understood to be important because the wire pulling member of a typical wire pull tester has a limited displacement range. By way of example, a support fixture used with a large semiconductor device may be unsatisfactory for a small semiconductor device because such a support fixture will not have sufficient height to hold the device within the displacement range of the tester's wire pulling member.

One known solution to this problem involves providing a different support fixture for each type of semiconductor device. It can be readily appreciated that this solution is inconvenient for an operator who is generally required to test many different types of semiconductor devices, thus requiring use of many different support fixtures. Another proposed solution which has similar deficiencies requires restraining the device under test to a support using a clamp. Different clamp configurations, however, must be provided to accommodate semiconductor devices that vary with respect to size, shape, and configuration. Furthermore, a clamp may not be convenient or useful when the device is very small or very thin.

Another cumbersome yet often used approach requires the operator to manually hold the device during the wire pull test. During the test, the operator must operate the wire pull testing apparatus, which typically involves the use of a microscope or other magnification apparatus needed to coordinate the delicate testing procedure. It can be appreciated that manually holding the device in place during the wire pull test is both inconvenient and problematic.

An advantage realized by employing a support fixture in accordance with the present invention concerns a significant increase in wire pull testing efficiency and convenience. Employing a single adaptable support fixture for use with a wide variety of semiconductor devices obviates the need for customized fixtures which are uniquely suited for specific device types.

Figure 5A:
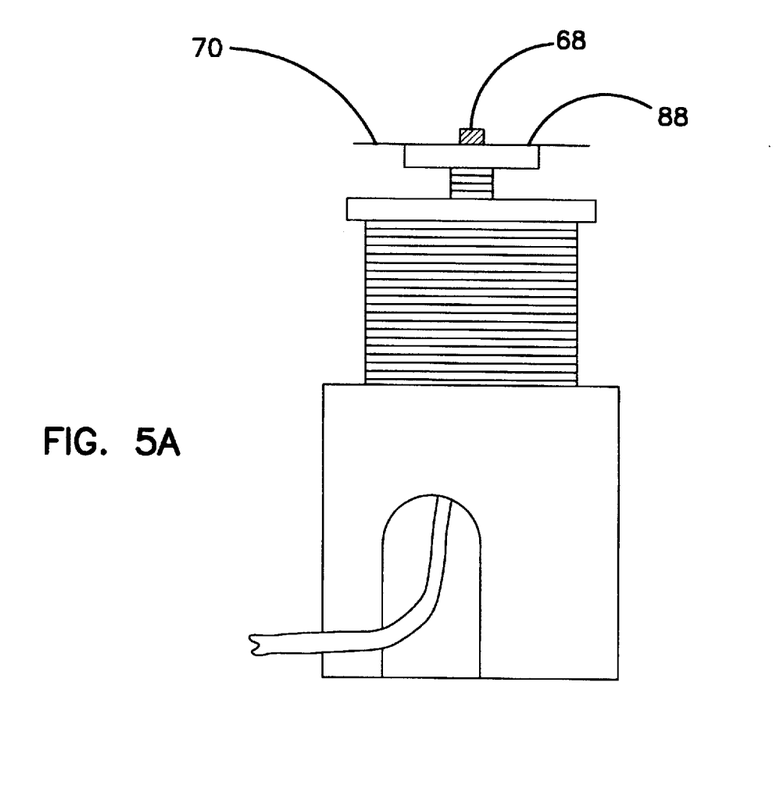
FIG. 5a is a side elevational view of fixture supporting a flat pack semiconductor device.
Figure 5B:
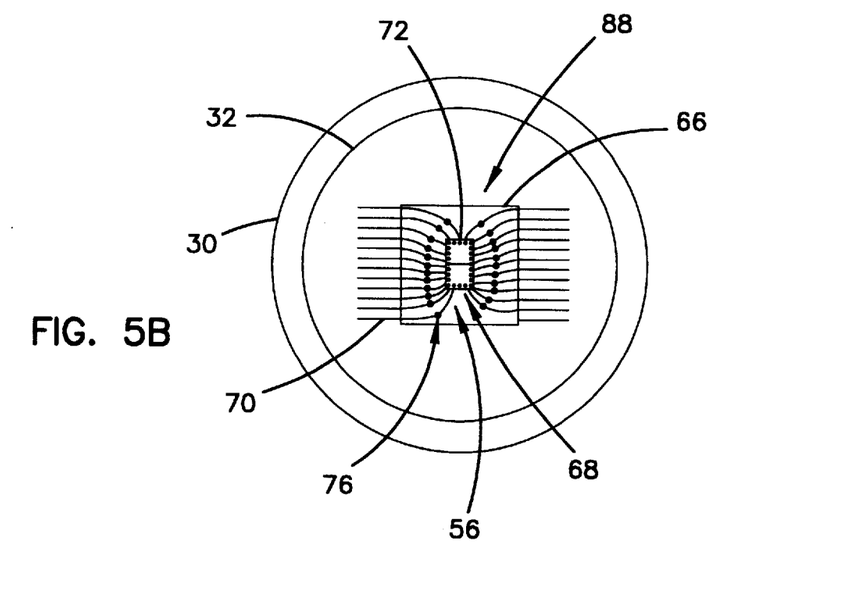
FIG. 5b is a top view of the flat pack semiconductor device of FIG. 5a being supported by the fixture.

Referring to FIGS. 5a and 5b, the fixture 20 is depicted supporting a flat pack semiconductor device 88, which is characterized by leads 70 extending outwardly in a horizontal direction from device 88. The semiconductor device 88 depicted in FIGS. 5a and 5b includes a chip carrier 66, a die 68, and a number of leads 70. The chip carrier 66 defines a portion of a casing (not shown) which surrounds the die 68 and protects the die 68 from damage and degradation from external sources.

The die 68 contains the active electronic components of the semiconductor device 88. Die bonding pads 72 are embedded in the die 68 and connected to the electronic components formed in the semiconductor material of the die 68. The leads 70 terminate at lead pads 76 which are arranged on the chip carrier 66. The die bonding pads 72 and lead pads 76 are connected to one another by wires 56. A wire 56 will typically connect one or more die bonding pads 72 to one or more lead pads 76 as determined by the desired lead configuration for a particular semiconductor device 88. These wires are typically constructed of aluminum, although other materials are also used. The object of the wire pull test is to determine the bond strength of the connections between the wire 56 and the various electrical contacts of the semiconductor device 88 connected to the wire 56.

Figure 6A:
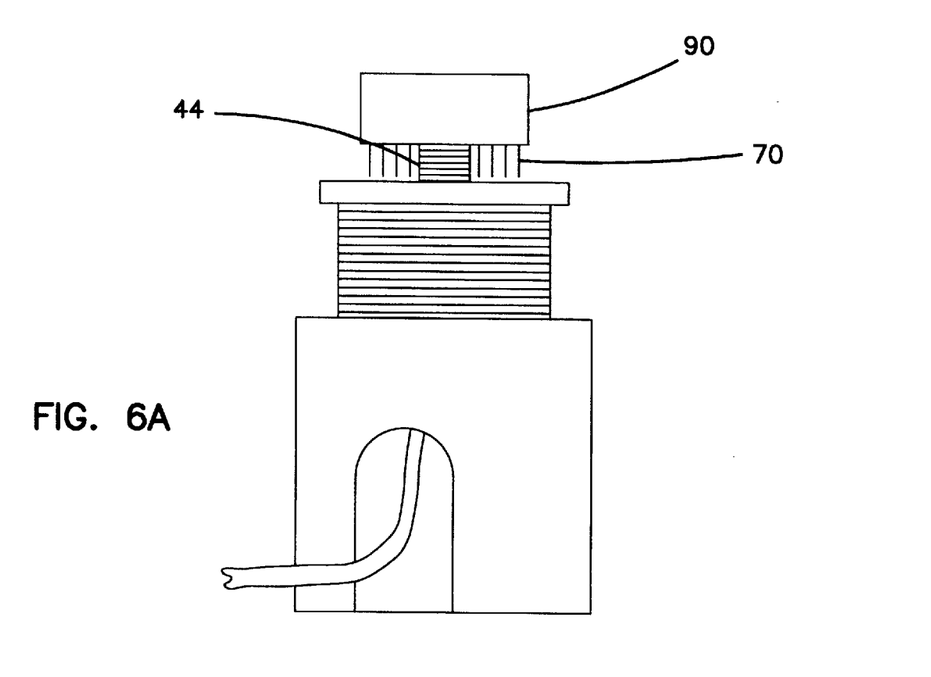
FIG. 6a is a side elevational view of a fixture supporting a semiconductor device of the pin grid array (PGA) type.
Figure 6B:
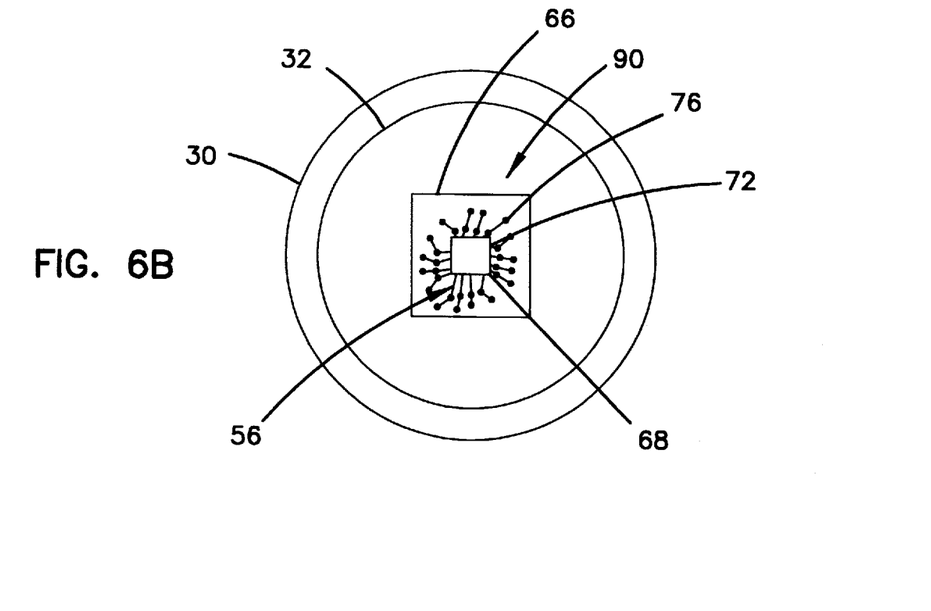
FIG. 6b is a top view of the PGA semiconductor device of FIG. 6a being supported by the fixture.

Other types of semiconductor devices have similar components which may be arranged differently to achieve desired functionality. FIGS. 6a and 6b depict the fixture 20 supporting a semiconductor device 90 of the pin grid array (PGA) type. The PGA semiconductor device 90 has leads 70 which extend perpendicularly from a surface of device 90. PGA type semiconductor devices can have more than 300 leads per device. PGA semiconductor devices 90, like flat pack devices 88, have a chip carrier 66, a die 68, a number of leads 70, die bonding pads 72 attached to the die 68, and lead pads 76 which are attached to the leads 70. Wires 56 connect the die bonding pads 72 to the lead pads 76.

As is shown in FIG. 6a, the PGA semiconductor device 90 is configured so that the leads 70 extend outwardly from the device 90 towards the fixture 20 when the device 90 is mounted on the mounting surface 24 of the fixture 20. In accordance with one embodiment of the invention, the mounting surface 24 is configured so that the leads 70 do not touch any portion of the fixture 20. This configuration will ensure that a surface of the semiconductor device 90 is in contact with the mounting surface 24 during the wire pull test, and that the leads 70 remain undamaged.

Figure 7A:
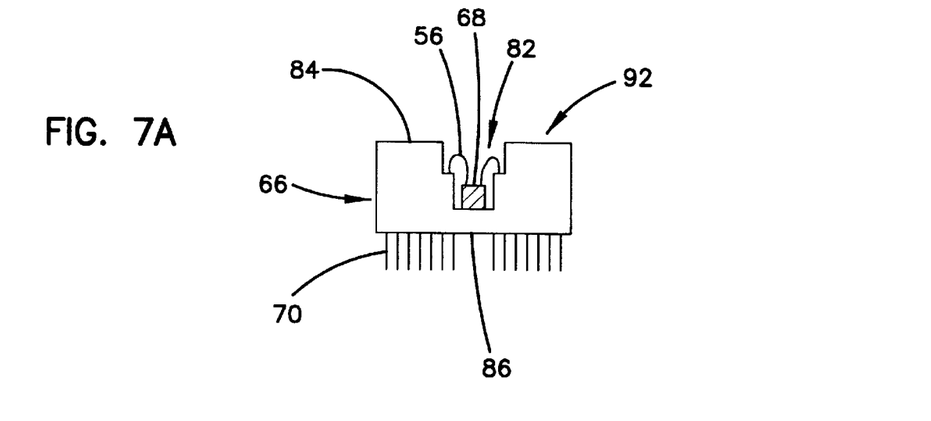
FIG. 7a is a cross-sectional view of a cavity-up PGA semiconductor device.
Figure 7B:
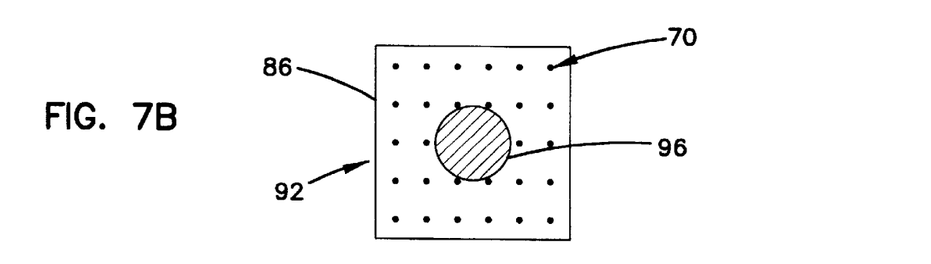
FIG. 7b is a bottom view of the semiconductor device of FIG. 7a showing a region of contact between the semiconductor device and a mounting surface and a port provided on the fixture shown in FIG. 2.
Figure 8A:
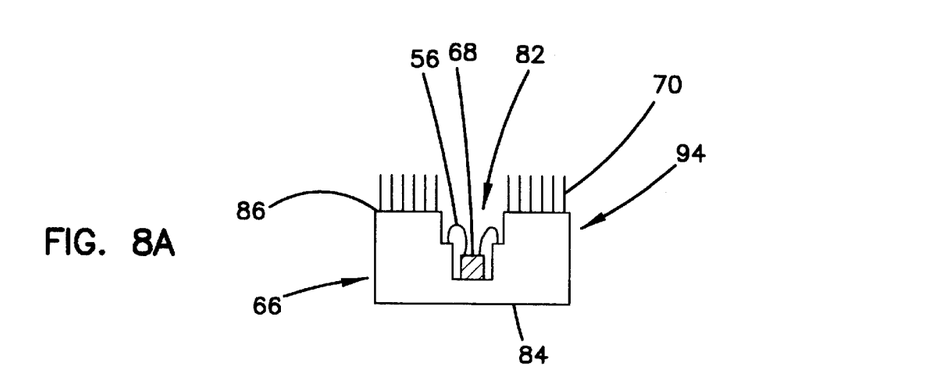
FIG. 8a is a cross-sectional view of a cavity-down PGA semiconductor device.
Figure 8B:
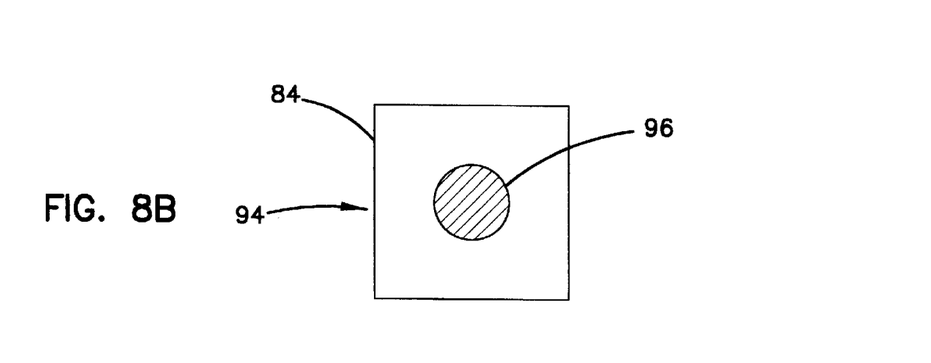
FIG. 8b is a top view of the semiconductor device of FIG. 8a showing a region of contact between the semiconductor device a mounting surface and a port of the fixture shown in FIG. 2.

FIGS. 7 and 8 depict cross-sections of PGA type semiconductor devices. FIG. 7a depicts a cavity-up PGA semiconductor device 92. In cavity-up devices 92, the die 68 is affixed within a cavity 82 provided in the upper surface 84 of the chip carrier 66. The leads 70 of the cavity-up semiconductor device 92 penetrate the chip carrier 66 and extend perpendicularly from the lower surface 86 of chip carrier 66. FIG. 8a depicts a cavity-down PGA device 94. In this device, the die 66 is affixed within a cavity 84 provided on the lower surface 86 of the chip carrier 66. The leads 70 penetrate the chip carrier 66 and extend perpendicularly from the lower surface 86 of the chip carrier 66.

FIGS. 7b and 8b depict a region 96 of the semiconductor devices 92 and 94, respectively, all or part of which is in contact with the mounting surface 24 and proximate to the port 26 of the fixture 20 during the wire pull test. In the case of cavity-up devices 92, as depicted in FIG. 7b, the mounting surface 24 is in contact with lower surface 86 of the device 92. In the case of cavity down devices 94, as depicted in FIG. 8b, the mounting surface 24 is in contact with the upper surface 84 of the device 94. In both cases, the die 68 and wires 56 are exposed, and are in a proper orientation for the wire pull test.

Referring now to FIG. 4, the embodiment of the fixture 20 depicted in FIGS. 2 and 3 is shown in operation with a wire pull tester 52. The wire pull tester 52 illustrated in FIG. 4 is a depiction of one type of wire pull tester, and is similar to a tester produced by UNITEK Equipment Division, Model No. Micropull® III Wire Bond Pull Tester. Those skilled in the art will recognize that the fixture 20 of the present invention can be used with other wire pull testers having configurations which differ from that depicted in FIG. 4.

The tester 52 includes a tester stand 64, a tester arm 60 attached to the stand 64, and a wire pulling member 54 attached to one end of the tester arm 60. The wire pulling member 54 is configured to engage a wire 56 of the semiconductor device 28. The wire pulling member 54 may be a hook, a needle, a clamp, or other known device which can engage the wire 56 during the wire pull test and transmit a pull force to the connections between the wire 56 and the die bonding pads 72 and lead pads 76. When activated, the tester 52 moves the wire pulling member 54 which, in turn, exerts a pull force on the wire 56. The tester 52 typically employs a measuring device (not shown) that measures the amount of force applied to arm and, therefore, to the wire 56. It is noted that a test viewer 62 is provided so that an operator can view a magnified image of the region surrounding and including the wire 56 subjected to the pull test.

Referring to the Drawings in general and to FIG. 4 in particular, a procedure for using the fixture 20 in a wire pull test is provided as follows. A semiconductor device 28 is selected for the test, and the die 68, wire 56, and both the die bonding pad 72 and the lead pad 76 connected to the wire 56 are exposed. The semiconductor device 28 is placed on the mounting surface 24 of the fixture 20. The fixture 20 is placed on a tester stand 64 or otherwise positioned under the wire pulling member 54 of the tester 52. The height of the fixture 20 is then adjusted using the height adjustment mechanism of the device support 22 to bring the wire 56 into proximity of the wire pulling member 54 of wire pull tester 52. It is noted that the height adjustment mechanism may be manually, mechanically, or electro-mechanically actuated. It is further noted that a computer controlled electro-mechanical height adjustment mechanism may be desirable when a high degree of precision is required.

An air pressure differential is provided at the port 26 of the mounting surface 24 so that the semiconductor device 28 firmly engages, and is restrained on, the mounting surface 24 of the fixture 20. The wire pulling member 54 is brought into engagement with the wire 56. A force is then applied to the tester arm 60 and to the wire pulling member 54 in a direction away from the device 28. This force is imparted to the connections between the wire 56 and the die bonding pad 72 and lead pad 76 by the engagement between the wire 56 and the wire pulling member 54.

In a destructive wire pull test, the pull force is increased until there is a mechanical failure indicated by either the wire 56 breaking or the wire 56 becoming disengaged from the die bonding pad 72 or the lead pad 76. In order to accurately determine the occurrence of mechanical failure or catastrophic fatigue, an operator typically observes a magnified image of the wire pulling member 54, wire 56, and both pads 72 and 76 subjected to the test through the test viewer 62.

The force at which mechanical failure or unacceptable fatigue occurs is determined by reading the force level provided by the force measuring device (not shown). The test is considered a success if the measured force exceeds a predetermined force value required by the specification for the semiconductor device under test, otherwise, the test is considered a failure. A predetermined number of wires for a prescribed number of semiconductor devices as detailed in a customer's specification are tested in this manner for each lot of semiconductor devices. The lot is approved if the number of successful tests exceeds a predetermined acceptance level given in the specification.

The previously described embodiments of the present invention have many advantages over conventional support approaches. One important advantage is that the height of the fixture 20 can be adjusted to bring the wire 56 affixed to the semiconductor device 28 into contact with wire pulling member 54 of wire pull tester 52. Because the semiconductor devices have varying sizes, shapes, and configurations, a single fixed height support fixture cannot be used for all such semiconductor devices. The adjustability of the height of the fixture 20 advantageously provides for the use of the fixture 20 in conjunction with a wide variety of semiconductor devices, and eliminates dependency on multiple fixed height fixtures.

Another advantage of the present invention is the provision of an air pressure differential at the port 26 of the fixture 20. This difference in pressures at the two surfaces 27 and 29 of the semiconductor device 28 creates a net force on the semiconductor device 28 which provides secure engagement between the device 28 and the mounting surface 24 of the fixture 20 without the need for additional hardware, such as a clamp, or manual restraint of the device 28 by the operator.

In accordance with one embodiment of the present invention, the air pressure differential provides a net force that exceeds an opposing force provided by the wire pull tester 52. In another embodiment, the air pressure differential provides a net force that exceeds the force required to either break the wire 56 or break the bond between the wire 56 and either the die bonding pad 72 or lead pad 76. In yet another embodiment, the air pressure differential provides a net force that exceeds a force specified in a commercial or military specification. In still a further embodiment of the present invention, the air pressure differential provides a net force that exceeds a two gram opposing force produced by the wire pull tester 52 in accordance with Military Specification 883, Method 2011.

It will, of course, be understood that various modifications and additions can be made to the embodiments discussed hereinabove without departing from the scope or spirit of the present invention. By way of example, the disclosed fixture may be employed to provide secure engagement between the fixture and a wafer or other semiconductor substrate having bond wires or other electrical leads disposed thereon. Accordingly, the scope of the present invention should not be limited by the particular embodiments described above, but should be defined only by the claims set forth below and equivalents thereof.

What is claimed is:

1. A fixture for use with a tester having a wire pulling member, which tests the strength of a bond between an electrical contact of a semiconductor device and a wire affixed to the electrical contact, comprising:

a device support;

a mounting surface provided on the device support, wherein the mounting surface has an area that is less than an area of a surface of the semiconductor device, whereby the semiconductor device extends laterally beyond the mounting surface when mounted on the fixture; and a port provided at the mounting surface of the device support with which an air pressure differential is produced to maintain engagement between the mounting surface and the surface of the semiconductor device.

2. The fixture of claim 1, wherein the device support includes a height adjustment mechanism to adjust the height of the mounting surface to permit engagement between the wire of the semiconductor device and the wire pulling member of the tester.

3. The fixture of claim 2, wherein the device support comprises a lower support section and an upper support section engaging the lower support section, wherein the engagement between the lower support section and the upper support section is alterable to permit engagement between the wire of the semiconductor device and the wire pulling member of the tester.

4. The fixture of claim 3, wherein the engagement between the lower support section and the upper support section is rotatably alterable to permit engagement between the wire of the semiconductor device and the wire pulling member of the tester.

5. The fixture of claim 1, wherein the air pressure differential is produced by a vacuum pump coupled to the port.

6. The fixture of claim 5, further comprising a valve, operable between an open position and a closed position, coupled to the port and the vacuum pump such that when the valve is in the open position, the vacuum pump provides the air pressure differential at the port, and when the valve is in the closed position, the vacuum pump is isolated from the port.

7. The fixture of claim 6, wherein the air is introduced to the port when the valve is in the closed position to decrease the air pressure differential.

8. The fixture of claim 1, wherein the air pressure differential maintains the engagement between the mounting surface and the surface of the semiconductor device when a pull force provided by a wire pulling member exceeds a strength of the bond between the wire and the electrical contact of the semiconductor device.

9. The fixture of claim 1, wherein the air pressure differential maintains the engagement between the mounting surface and the surface of the semiconductor device when a pull force provided by a wire pulling member exceeds a fatigue strength of the wire.

10. The fixture of claim 1, wherein the air pressure differential maintains the engagement between the mounting surface and the surface of the semiconductor device when a pull force provided by a wire pulling member is at least as large as a force specified in a military or commercial semiconductor device specification.

11. The fixture of claim 1, wherein the air pressure differential maintains the engagement between the mounting surface and the surface of the semiconductor device when a pull force provided by a wire pulling member is approximately 2 grams.

12. An apparatus for performing a wire pull test, comprising:
a tester including a wire pulling member;
a semiconductor device; and
a device support for holding the semiconductor device during the test, comprising:
a stand;
a mounting surface provided on the stand, wherein the mounting surface has an area that is less than an area of a surface of the semiconductor device, whereby the semiconductor device extends laterally beyond the mounting surface when mounted on the fixture; and
a port provided at the mounting surface of the stand with which an air pressure differential is produced to maintain engagement between the mounting surface and a surface of the semiconductor device.

13. The apparatus of claim 12, wherein the stand includes a height adjustment mechanism to adjust the height of the mounting surface to permit engagement between a wire of the semiconductor device and the wire pulling member of the tester.

14. The fixture of claim 13, wherein the stand comprises a lower support section and an upper support section engaging the lower support section, wherein the engagement between the lower support section and the upper support section is alterable to permit engagement between the wire of the semiconductor device and the wire pulling member of the tester.

15. The fixture of claim 14, wherein the engagement between the lower support section and the upper support section is rotatably alterable to permit engagement between the wire of the semiconductor device and the wire pulling member of the tester.

16. The apparatus of claim 12, wherein the air pressure differential is produced by a vacuum pump coupled to the port.

17. The apparatus of claim 16, further comprising a valve, operable between an open position and a closed position, coupled to the port and the vacuum pump such that when the valve is in the open position, the vacuum pump provides the air pressure differential at the port, and when the valve is in the closed position, the vacuum pump is isolated from the port.

18. The apparatus of claim 17, wherein the air is introduced to the port when the valve is in the closed position to decrease the air pressure differential.

19. The apparatus of claim 12, wherein the air pressure differential maintains the engagement between the mounting surface and the surface of the semiconductor device when a pull force provided by a wire pulling member exceeds a strength of the bond between the wire and the electrical contact of the semiconductor device.

20. The apparatus of claim 12, wherein the air pressure differential maintains the engagement between the mounting surface and the surface of the semiconductor device when a pull force provided by a wire pulling member exceeds a fatigue strength of the wire.

21. The fixture of claim 1, wherein the device support comprises a mounting column extending from the device support and including the mounting surface.

22. The fixture of claim 21, wherein the device support further comprises a mounting column adjustment mechanism to permit adjustment of a distance that the mounting column extends from the device support.

23. The fixture of claim 22, wherein the distance that the mounting column extends from the device support is adjustable by rotating the mounting column relative to the device support.

24. The apparatus of claim 12, wherein the stand comprises a mounting column extending from the stand and including the mounting surface.

* * * * *